(12) United States Patent
Li et al.

(10) Patent No.: US 11,672,995 B2
(45) Date of Patent: Jun. 13, 2023

(54) SHAPE MEMORY MATERIAL-BASED MINIMALLY INVASIVE IMPLANTATION WITH MULTI-AXIS CURL SELF-EXPANDING STRUCTURE

(71) Applicant: TSINGHUA UNIVERSITY, Beijing (CN)

(72) Inventors: Luming Li, Beijing (CN); Linze Li, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 1020 days.

(21) Appl. No.: 16/463,995

(22) PCT Filed: Dec. 18, 2017

(86) PCT No.: PCT/CN2017/117000
§ 371 (c)(1),
(2) Date: May 24, 2019

(87) PCT Pub. No.: WO2018/166259
PCT Pub. Date: Sep. 20, 2018

(65) Prior Publication Data
US 2020/0384275 A1    Dec. 10, 2020

(30) Foreign Application Priority Data
Mar. 14, 2017    (CN) .......................... 201710149321.1

(51) Int. Cl.
*A61N 1/378*    (2006.01)
*A61N 1/375*    (2006.01)
(Continued)

(52) U.S. Cl.
CPC ............ *A61N 1/3787* (2013.01); *A61B 90/39* (2016.02); *A61B 90/90* (2016.02); *A61F 2/0063* (2013.01);
(Continued)

(58) Field of Classification Search
CPC . A61F 2/0063; A61F 2/844; A61F 2210/0014
See application file for complete search history.

(56) References Cited

U.S. PATENT DOCUMENTS

| 4,602,624 A | 7/1986 | Naples et al. |
| 6,764,514 B1 * | 7/2004 | Li ........................... A61F 2/441 |
| | | 623/17.12 |

(Continued)

FOREIGN PATENT DOCUMENTS

| CN | 200980690 Y | 11/2007 |
| CN | 104548345 A | 4/2015 |

(Continued)

OTHER PUBLICATIONS

International Search Report dated Mar. 14, 2018 in corresponding International Application No. PCT/CN2017/117000; 5 pages.

*Primary Examiner* — Todd J Scherbel
(74) *Attorney, Agent, or Firm* — Grossman Tucker Perreault & Pfleger, PLLC

(57) ABSTRACT

A shape memory material-based minimally invasive implantation with multi-axis curl self-expanding structure, and an implant having said structure: the implant comprises an actuating member, and the implant has a first shape and a second shape, the second shape having a larger area than that of the first shape; the implant is provided with a plurality of curling portions, and the actuating member may cause a curling portion to expand along a curling axis thereof, thereby transforming the implant from the first shape to the second shape. Different self-expanding structures may be designed by using the elasticity and memory effect of shape memory materials. Deploying functional modules, such as a circuit, a battery, a sensor, an energy collector and the like, on the structures may achieve more functions.

12 Claims, 4 Drawing Sheets

(a)

(b)

(51) Int. Cl.
 *A61N 1/05* (2006.01)
 *A61F 2/844* (2013.01)
 *A61F 2/00* (2006.01)
 *A61B 90/00* (2016.01)
 *A61B 90/90* (2016.01)

(52) U.S. Cl.
 CPC ............ *A61F 2/844* (2013.01); *A61N 1/0534* (2013.01); *A61N 1/3756* (2013.01); *A61B 2560/0219* (2013.01); *A61F 2210/0004* (2013.01); *A61F 2210/0014* (2013.01); *A61F 2210/0076* (2013.01); *A61F 2230/0091* (2013.01)

(56) References Cited

U.S. PATENT DOCUMENTS

| | | | | |
|---|---|---|---|---|
| 8,617,188 | B2* | 12/2013 | Dudai | A61B 17/0057 |
| | | | | 623/23.72 |
| 2008/0057100 | A1 | 3/2008 | Williams et al. | |
| 2009/0240267 | A1* | 9/2009 | Crawley | A61F 2/0063 |
| | | | | 606/151 |
| 2013/0035704 | A1* | 2/2013 | Dudai | A61F 2/0063 |
| | | | | 606/151 |
| 2013/0331868 | A1* | 12/2013 | LePage, Jr. | A61F 2/0063 |
| | | | | 606/151 |
| 2013/0338767 | A1* | 12/2013 | Mazzocchi | A61F 2/1635 |
| | | | | 623/6.22 |
| 2018/0318068 | A1* | 11/2018 | Otts | A61L 27/50 |

FOREIGN PATENT DOCUMENTS

| | | |
|---|---|---|
| CN | 105213066 A | 1/2016 |
| CN | 106955420 A | 7/2017 |
| CN | 106974743 A | 7/2017 |

\* cited by examiner

SHAPE MEMORY MATERIAL-BASED MINIMALLY INVASIVE IMPLANTATION WITH MULTI-AXIS CURL SELF-EXPANDING STRUCTURE This application claims all benefits from China Patent Application No. 201710149321.1, titled "SHAPE MEMORY MATERIAL-BASED MINIMALLY INVASIVE IMPLANTATION WITH SELF-EXPANDING MULTI-AXIS CURL STRUCTURE", filed on Mar. 14, 2017, in the China Intellectual Property Office, the disclosure of which is incorporated herein by reference.

FIELD

This invention relates to a shape memory material-based minimally invasive implantation with multi-axis curl self-expanding structure, belong to implantable medical device (IMD) technology field.

BACKGROUND

Implantable medical device generally refers to a medical device that is partly or entirely implanted into the human body or natural canal by means of surgery. After the operation, the implantable medical device will stay in the body for a long time, usually for at least 30 days. Implanted medical device belongs to the high-end products of the third category of medical devices and is an important product in the medical device industry. Currently, the implanted medical devices, that are widely applied, can be active and passive implantable medical devices, such as heart pacemakers, defibrillators, deep brain stimulation (DBS), stents, catheters, artificial valves, artificial cochlea, artificial blood vessels, intraocular lenses, artificial hip joints, artificial knee joints, bone plates, bone nails and other implants.

In the process of medical device implantation, it is inevitable to cut an incision, so that the medical device can be implanted into the body. On the one hand, the relatively larger incision may cause greater surgical risk to patients during the operation. On the other hand, the relatively larger incision also may cause greater chance of infection and pain after the operation. Therefore, what is needed is a structure that can be implanted into the body through a relatively smaller incision, expand to have a larger surface, and deployed to a larger area after implantation, so that to achieve the required function.

SUMMARY

A shape memory material-based minimally invasive implantation with multi-axis curl self-expanding structure, comprises a shape memory self-expanding structure and a functional module. The shape memory self-expanding structure consists of shape memory material and is in first shape before being implanted in body. The implant can be transformed from the first shape to the second shape. The second shape has a larger area than that of the first shape. Based on the elasticity and/or memory effect of the shape memory material, the self-expanding structure is a small size structure before being implanted and would be caused to expand to be a large size structure and deployed on a larger area after being implanted by the releasing constraint, changing temperature, light illumination, electromagnetic irradiation, or chemical induce. The functional module can include circuit, battery, sensor, energy collector or other device.

An implant is provided in this invention. The implant comprises: an actuating member, wherein the implant has a first shape and a second shape, the second shape having a larger area than that of the first shape; the implant comprises a plurality of curling portions, and the actuating member is capable of causing the plurality of curling portions to expand along curling axes thereof, so that the implant is transformed from the first shape to the second shape.

Furthermore, the number of the plurality of curling portions is greater than two, and the curling axes are parallel with or nonparallel with each other.

Furthermore, the number of the plurality of curling portions is greater than three; the implant further comprises a central body portion, and the plurality of curling portions are substantially symmetrically arranged around the central body portion.

Furthermore, the plurality of curling portions are in curled state when the implant is in the first shape, the plurality of curling portions are in expanded state when the implant is in the second shape, and the second shape is substantially the rectangular.

Furthermore, the implant further comprises a functional module.

Furthermore, the functional module comprises a wireless energy transfer unit.

Furthermore, the actuating member comprises a shape memory material-based frame.

Furthermore, the implant further comprises a constraint unit configured to keep the implant in the first shape.

Furthermore, the constraint unit is made of biodegradable material.

Furthermore, the wireless energy transfer unit is selected from photovoltaic cell array, piezoelectric electric generator, friction electric generator, thermoelectric electric generator, electromagnetic electric generator, and vibration electric generator.

Furthermore, the wireless energy transfer unit is an photovoltaic cell array, and the photovoltaic cell array forms a single layer or a plurality of layers, and a separating membrane is located or not located between adjacent two layers.

Furthermore, the outer surface of the wireless energy transfer unit is coated by at least one biocompatible film Furthermore, at least one of the actuating member and the wireless energy transfer unit defines one or more than one through hole.

Furthermore, the implant comprises a plurality of units, the plurality of units are connected with each other by conductive wires, and each unit comprises the actuating member and the functional module.

An implantable medical device is also provided. The implantable medical device comprises: the implant provided above and an implantable main portion, and the implant and the implantable main portion are connected with each other by conductive wire.

DETAILED DESCRIPTION

References will now be made to the drawings to describe, in detail, various embodiments of the shape memory material-based minimally invasive implantation with multi-axis curl self-expanding structures provided by this invention.

The shape memory material has the properties of elasticity and memory effect. By changing the constraints, temperature, light illumination, electromagnetic irradiation, chemical induction, and other external conditions, it can make the shape memory material realize structural automatic self-transformation. The specific using method includes but not limited to:

Elastic self-expanding type

Based on the elasticity of the shape memory material, the shape memory material is first constrained by compressing, and then the constraint is released after being implanted in body, so that the shape memory material realizes self-expanding.

Memory effect self-expanding type

Based on the memory effect of the shape memory material, the shape memory material is first soaked in disinfecting ice water, and then the shape memory material is heated by body temperature to expand after being implanted in body.

Memory effect and heating expanding type

Based on the memory effect of the shape memory material, after being implanted in body, the shape memory material is heated (illuminated by light, irradiated by electromagnetic wave, or chemical induced to expand. The heating method can be radio frequency, injecting hot physiological saline solution after being implanted, or electrical heating etc.

Memory effect and heating shrinking removing type

After being implanted in body, the shape memory material expand due to balloon. Before removing out of the body, the shape memory material is heated (illuminated by light, irradiated by electromagnetic wave, or chemical induced) to shrink.

The shape memory material-based minimally invasive implantation with multi-axis curl self-expanding structures provided in this invention can be designed to be different self-expanding structures based on the elasticity and memory effect of the shape memory material. The functional module, such as circuit, battery, sensor, energy collector etc., can be deployed on the self-expanding structure so that the self-expanding structure can have more functions.

The shape memory material-based minimally invasive implantation with multi-axis curl self-expanding structures provided in this invention are described in following embodiments.

Embodiment 1

Figure 1:
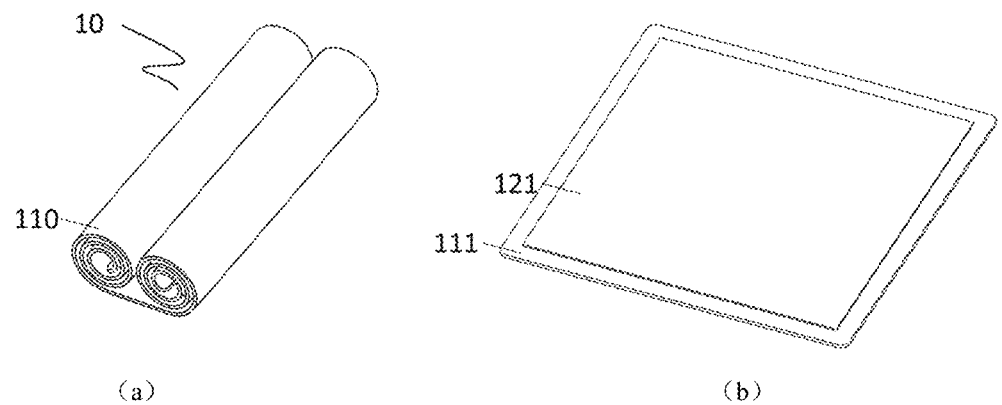
FIG. 1 is a structural schematic view of embodiment 1 of this invention.

Referring to FIG. 1, the shape memory material-based minimally invasive implantation with multi-axis curl self-expanding structure 10 includes a shape memory material-based frame 110 and a functional module 120 (not shown). The functional module 120 is deployed on the shape memory material-based frame 110. The shape memory material-based frame 110 is in bi-axis curled state before being implanted. FIG. 1(a) shows the shape of the self-expanding structure 10 before being implanted in body, which has a small size, so that it is easy for minimally invasive implantation. FIG. 1(b) shows the shape of the self-expanding structure 10 after being implanted in body, the number 111 represents the expanded shape memory material-based frame which is in plane (can be different shape), the number 121 represents the implanted functional module. After being implanted in body, the entire self-expanding structure 10 can be deployed in a larger area.

Embodiment 2

Figure 2:
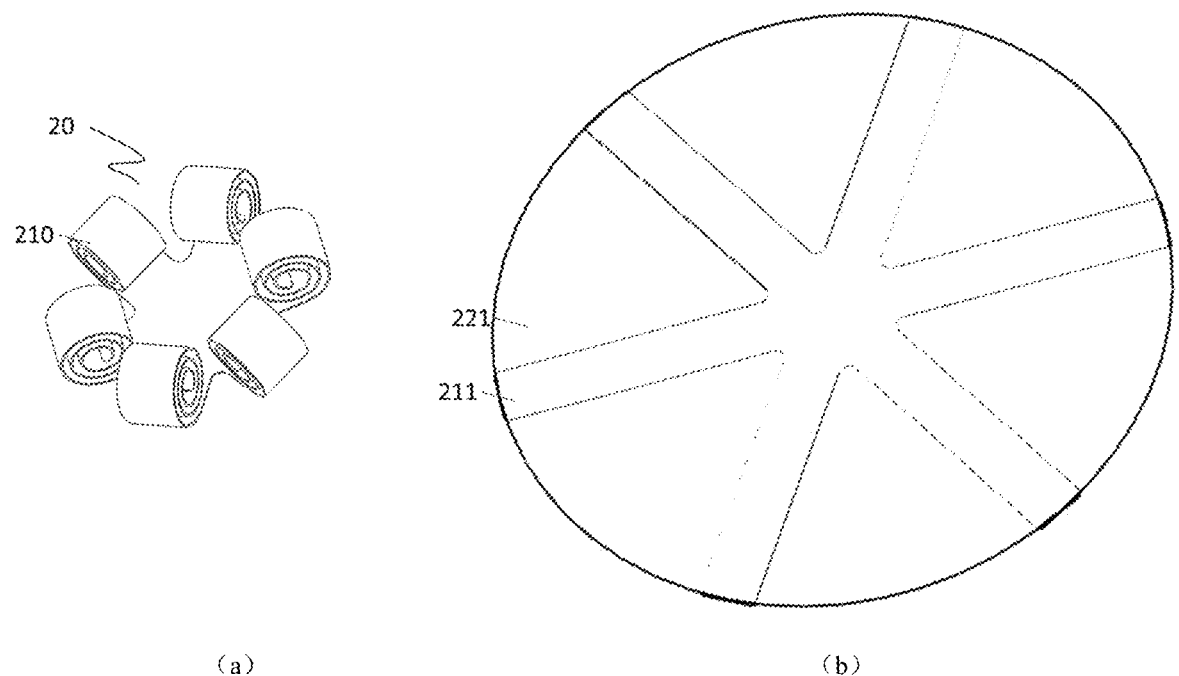
FIG. 2 is a structural schematic view of embodiment 2 of this invention.

Referring to FIG. 2, the shape memory material-based minimally invasive implantation with multi-axis curl self-expanding structure 20 includes a shape memory material-based frame 210 and a functional module 220 (not shown). The functional module 220 is coated on the shape memory material-based frame 210. The shape memory material-based frame 210 is in six-axis curled state (can be n-axis, "n" is a natural number) before being implanted. FIG. 2(a) shows the shape of the self-expanding structure 20 before being implanted in body, which has a small size, o that it is easy for minimally invasive implantation. FIG. 2(b) shows the shape of the self-expanding structure 20 after being implanted in body, the number 211 represents the expanded shape memory material-based frame, the six-axis curl structure expands to be in the same plane (can be different shape), and the number 221 represents the implanted functional module. After being implanted in body, the entire self-expanding structure 20 can be deployed in a larger area.

Embodiment 3

Figure 3:
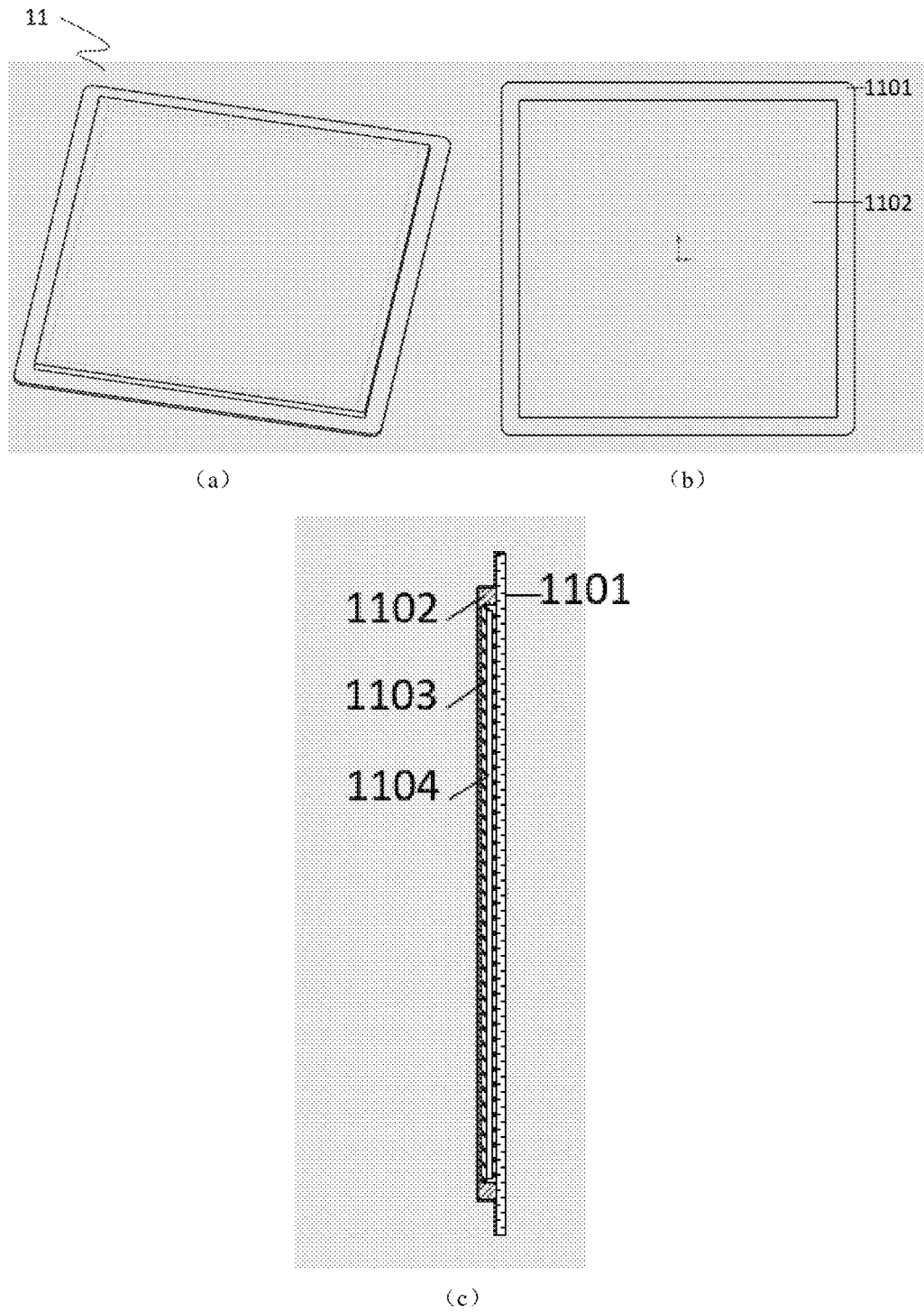
FIG. 3 is a structural schematic view of embodiment 3 of this invention.

Referring to FIG. 3, the shape memory material-based minimally invasive implantation with multi-axis curl self-expanding structure 11 includes a shape memory material-based frame 1101, a biocompatible flexible material 1102, a flexible sealing film 1103, and a functional module 1104. FIGS. 3(a), 3(b), 3(c) are respectively the 3-dimensional (3D) view of the expanded self-expanding structure 11, top view of the expanded self-expanding structure 11, and cross-sectional view of the expanded self-expanding structure 11. The functional module 1104 is deployed on the shape memory material-based frame 1101. The outer surface of the functional module 1104 is coated by the flexible sealing film 1103 and the biocompatible flexible material 1102. The flexible sealing film 1103 and the biocompatible flexible material 1102 respectively play the functions of sealing and improving biocompatibility.

Embodiment 4

Figure 4:
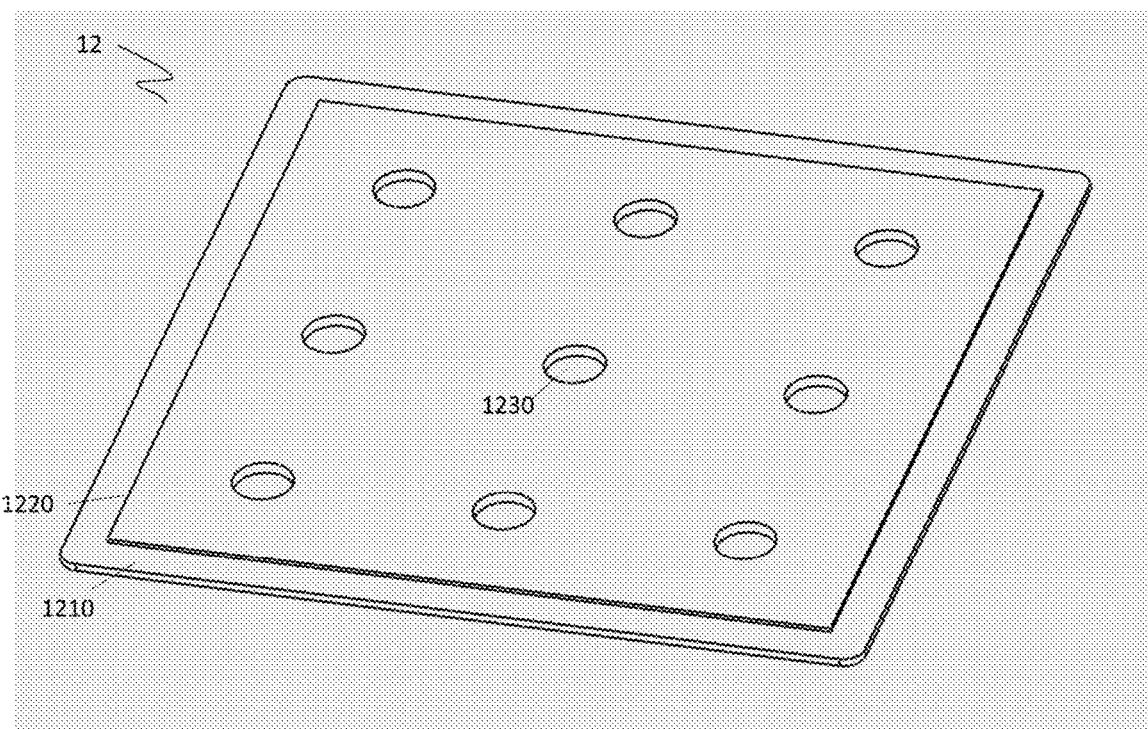
FIG. 4 is a structural schematic view of embodiment 4 of this invention.

Referring to FIG. 4, the shape memory material-based minimally invasive implantation with multi-axis curl self-expanding structure 12 includes a shape memory material-based frame 1210, a functional module 1220, and through holes 1230. The functional module 1220 is coated on the shape memory material-based frame 1210. The functional module 1220 has a larger surface area and may prevent the growth of the biological tissue. By forming some through holes 1230 on the functional module 1220, it is beneficial to the growth of biological tissues and the circulation of blood.

Embodiment 5

Figure 5:
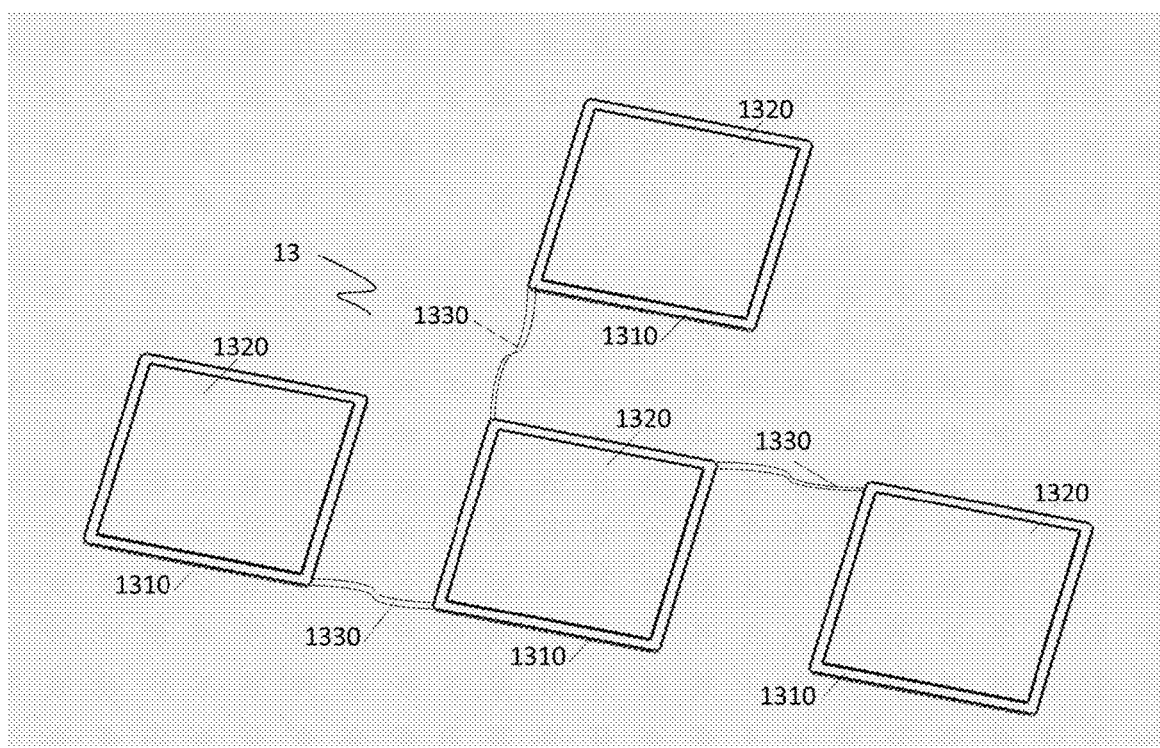
FIG. 5 is a structural schematic view of embodiment 5 of this invention.

Referring to FIG. 5, the shape memory material-based minimally invasive implantation with multi-axis curl self-expanding structure 13 includes a plurality of shape memory material-based frames 1310, and a plurality of functional modules 1320. The plurality of functional modules 1320 are deployed on the plurality of shape memory material-based frames 1310. The plurality of shape memory material-based frames 1310 and the plurality of functional modules 1320 are distributed at different positions and can be connected by conductive wires 1330.

Embodiment 6

Figure 6:
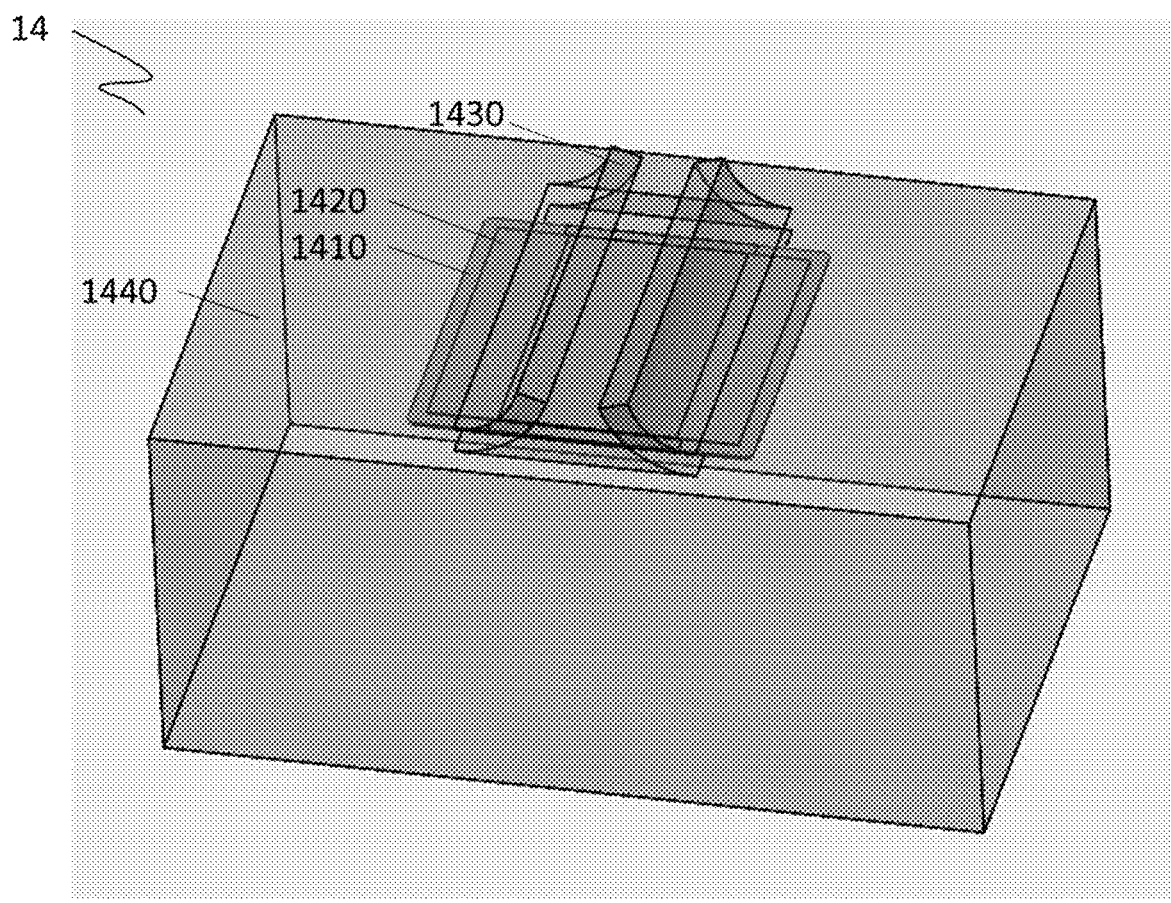
FIG. 6 is a structural schematic view of embodiment 6 of this invention.

Referring to FIG. 6, the shape memory material-based minimally invasive implantation with multi-axis curl self-expanding structure 14 includes a shape memory material-based frame 1410 and a functional module 1420. The functional module 1420 is deployed on the shape memory material-based frame 1410. The shape memory material-based minimally invasive implantation with multi-axis curl self-expanding structure 14 can be implanted at different subcutaneous positions. The number 1440 represents the skin at different positions (such as hands, neck, head etc.), the number 1430 represents the incision of the skin. Furthermore, when the functional module 1420 is a photovoltaic cell array, in order for receiving more light, the prefer position for the incision of the skin is the position where the light would not be sheltered by the wearing apparel (such as clothes, shoes, hat, etc.).

The above-described embodiments are only intended to illustrate some exemplary embodiments, which are described more specific and in more detail, but not to limit the scope of the claimed invention. For one of skilled in the art, any variations may be made to the embodiments without departing from the spirit of the disclosure, and the variations are also belong to the scope of the claimed invention. The scope of the claimed invention should be determined according to the claims.

The invention claimed is:

1. An implant, comprising: a shape memory material-based frame and a functional module, wherein the implant has a first shape and a second shape, the second shape having a larger area than that of the first shape, the implant comprises a plurality of curling portions, and the shape memory material-based frame is configured to cause the plurality of curling portions to expand along curling axes thereof, so that the implant is transformed from the first shape to the second shape; wherein the functional module comprises a wireless energy transfer unit; the wireless energy transfer unit is selected from the group consisting of photovoltaic cell array, piezoelectric electric generator, friction electric generator, thermoelectric electric generator, electromagnetic electric generator, and vibration electric generator; and the outer surface of the wireless energy transfer unit is coated by at least one biocompatible film.

2. The implant as claimed in claim 1, wherein the number of the plurality of curling portions is greater than two, and the curling axes are parallel with or nonparallel with each other.

3. The implant as claimed in claim 2, wherein the number of the plurality of curling portions is greater than three; the implant further comprises a central body portion, and the plurality of curling portions are substantially symmetrically arranged around the central body portion.

4. The implant as claimed in claim 1, wherein the plurality of curling portions are in a curled state when the implant is in the first shape, the plurality of curling portions are in an expanded state when the implant is in the second shape, and the second shape is rectangular.

5. The implant as claimed in claim 4, wherein at least one of the shape memory material-based frame and the wireless energy transfer unit defines one or more than one through hole.

6. The implant as claimed in claim 1, wherein the implant further comprises a constraint unit configured to keep the implant in the first shape.

7. The implant as claimed in claim 6, wherein the constraint unit is made of biodegradable material.

8. The implant as claimed in claim 1, wherein the wireless energy transfer unit is a photovoltaic cell array, and the photovoltaic cell array forms a single layer or a plurality of layers, and a separating membrane is located or not located between adjacent two layers.

9. The implant as claimed in claim 8, wherein at least one of the shape memory material-based frame and the wireless energy transfer unit defines one or more than one through hole.

10. The implant as claimed in claim 1, wherein at least one of the shape memory material-based frame and the wireless energy transfer unit defines one or more than one through hole.

11. The implant as claimed in claim 1, wherein the implant comprises a plurality of units, the plurality of units are connected with each other by conductive wires, and each unit comprises the shape memory material-based frame and the functional module.

12. An implantable medical device, comprising:
an implantable main portion; and
an implant, comprising:
a shape memory material-based frame and a functional module, wherein the implant has a first shape and a second shape, the second shape having a larger area than that of the first shape, the implant comprises a plurality of curling portions, and the shape memory material-based frame is configured to cause the plurality of curling portions to expand along curling axes thereof, so that the implant is transformed from the first shape to the second shape; wherein the functional module comprises a wireless energy transfer unit; the wireless energy transfer unit is selected from the group consisting of photovoltaic cell array, piezoelectric electric generator, friction electric generator, thermoelectric electric generator, electromagnetic electric generator, and vibration electric generator; and the outer surface of the wireless energy transfer unit is coated by at least one biocompatible film,
wherein the implant and the implantable main portion are connected with each other by conductive wire.

* * * * *